United States Patent [19]

Pettit et al.

[11] Patent Number: 5,393,897
[45] Date of Patent: Feb. 28, 1995

[54] ISOLATION AND STRUCTURE OF SPONGISTATINS 5,7,8 AND 9

[75] Inventors: George R. Pettit, Paradise Valley; Zbigniew A. Cichacz; Cherry L. Herald, both of Tempe, all of Ariz.

[73] Assignee: Arizona Board of Regents acting on behalf of Arizona State University, Tempe, Ariz.

[21] Appl. No.: 86,664

[22] Filed: Jul. 2, 1993

[51] Int. Cl.⁶ ........................................... C07D 323/00
[52] U.S. Cl. ..................................................... 549/267
[58] Field of Search ........................ 549/267; 514/450

[56] References Cited

U.S. PATENT DOCUMENTS 4,164,584  8/1979  Kupchan, deceased ............ 549/267
4,560,774  12/1985  Pettit et al. ........................ 549/267
4,833,257  5/1989  Pettit et al. ........................ 549/267
4,940,726  7/1990  Pettit et al. ........................ 514/450
4,996,229  2/1991  Moore et al. ....................... 514/450
5,096,922  3/1992  Reichenbach et al. ............. 514/450

Primary Examiner—C. Warren Ivy
Assistant Examiner—A. A. Owens
Attorney, Agent, or Firm—Richard R. Mybeck

[57] ABSTRACT

A Southwest Indian Ocean marine sponge *Spirastrella spinispirulifera* (bright colored reds and purples) has been found to contain new and exceptionally active cell (human cancer) growth inhibitors spongistatin 5, spongistatin 7, spongistatin 8 and spongistatin 9. These compositions are related to spongistatin 1, which was found in a black *Spongia sp.* in the Porifera family. A method of treating human cancer cells with spongistatin 5 and spongistatin 7 is also disclosed.

6 Claims, No Drawings

ISOLATION AND STRUCTURE OF SPONGISTATINS 5, 7, 8 AND 9

INTRODUCTION

The present invention relates to the discovery and isolation of compounds extracted from the marine sponge *Spirastrella spinispirulifera* (Class Demospongiae, Order Hadromerida, Family Spirastrellidae). These new macrocyclic lactones are designated herein as "spongistatin 5", "spongistatin 7", "spongistatin 8" and "spongistatin 9". Spongistatin 5 and spongistatin 7 were found to be remarkably potent and specific against the human cancer cell lines in the U.S. National Cancer Institute's panel. Some of the work described herein was supported by NCI Grant 01G CA-44344-01-04. The United States government may have certain rights to this invention.

BACKGROUND OF THE INVENTION

A great number of ancient marine invertebrate species in the Phyla Bryozoa, Mollusca and Porifera were well established in the earth's oceans over one billion years ago. Certainly such organisms have explored trillions of biosynthetic reactions in their evolutionary chemistry to reach present levels of cellular organization, regulation and defense. Marine sponges have changed minimally in physical appearance for nearly 500 million years, suggesting a very effective chemical evolution in response to changing environmental conditions for at least that time period. Some recognition of the potential for utilizing biologically potent marine animal constituents was recorded in Egypt about 2,700 BC, and by 200 BC sea hare extracts were being used in Greece for medicinal purposes. Such considerations, combined with the general observation that marine organisms (especially invertebrates and sharks) rarely develop cancer, led to the first systematic investigation of marine animal and plant anticancer constituents.

By 1968 ample evidence had been obtained, based on the U.S. National Cancer Institute's key experimental cancer systems, that certain marine organisms would provide new and structurally novel antineoplastic and-/or cytotoxic agents. Analogous considerations suggested that marine organisms could also provide effective new drugs for other severe medical challenges, such as viral diseases. Furthermore, marine organisms were expected to contain potentially useful drug candidates (and biochemical probes) of unprecedented structural types, that would have eluded discovery by contemporary techniques of medicinal chemistry. Fortunately, some of these expectations have been realized in the intervening period. Illustrative of these successes are the discoveries of the bryostatins, dolastatins, and cephalostatins by the Cancer Research Institute in Tempe, Ariz. where several members of these series of remarkable anticancer drug candidates are either now in human clinical trial or preclinical development. See: e.g. U.S. Pat. Nos. 4,816,444, 4,833,257, 4,873,245, and 4,879,278.

As is well known to those presently engaged in medical research, the time between the isolation of a new compound, and its introduction to the market place takes at least several years in the best case and can take several decades. Consequently, industry, in association with the government, has devised a number of qualifying tests which serve two purposes. One purpose is to eliminate those substances whose results in the qualifiers unequivocally demonstrate that the further expenditure of funds on developing those substances would be economically counter-productive. The second, and more important purpose, is to identify those substances which demonstrate a high likelihood of success and therefore warrant the requisite further investment necessary to obtain the data which is required to meet the various regulatory requirements imposed by those governments which regulate the market place into which such substances will enter.

The present cost of obtaining such data approaches Ten Million Dollars ($10,000,000 U.S.) per substance. Economics dictate that such an investment not be made unless there is a reasonable likelihood that it can be recovered. Absent such an opportunity, there will be no such investment, and without investment, the research requisite for the discovery of potentially life saving drugs will stop.

Only two hundred years ago, many diseases ravaged humankind. Many of these diseases now have been controlled or eradicated. In the development of the means to treat or control these diseases, work with the appropriate common experimental animals was of critical importance. With the various types of cancers, and with the HIV virus, such work is presently ongoing. The research for the treatment of various types of cancer is coordinated in the United States by the National Cancer Institute (NCI). NCI, as a government entity, has been charged with assisting anti-cancer research. To establish whether a substance has anti-cancer activity, NCI has established a variety of protocols, one of which involves testing the candidate substance against a cell line panel containing 60 human tumor cell lines. This protocol has been verified and is generally accepted throughout the scientific community. This protocol and the established statistical means of evaluating the results obtained therefrom have been fully described in the literature. See *Principles & Practice of Oncology* PPO Updates, Volume 3, Number 10, October 1989, by Michael R. Boyd, M.D., Ph.D., for an in depth description of the test protocol. The statistical analysis is explained in "Display and Analysis of Patterns of Differential Activity of Drugs Against Human Tumor Cell Lines: Development of Means Graph and COMPARE Algorithm" *Journal of the National Cancer Institute* Reports Vol. 81, No. 14, Pg. 1088, Jul. 14, 1989, by K. D. Paull et al. Both of these references are incorporated herein by this reference thereto. The effectiveness and validity of the NCI in vitro protocol continues to be verified.

Two newer references of note have been authored, in whole or in part by Dr. M. R. Boyd of the National Cancer Institute. The first is "Data Display and Analysis Strategies from the NCI disease Oriented in vitro Antitumor Drug Screen." Boyd, M. R. et al, in *Cytotoxic Anticancer Drug Models and Concepts for Drug Discovery and Development;* Valeriote, F. A., Corbett, T., Baker, L. Eds; Kluwer Academic Press: Amsterdam, 1992, pp 11–34. The second is "The Future of New Drug Development." Boyd, M. R. in *Current Therapy in Oncology;* Niederhuber, J. E., Ed. Mosby: St. Louis, 1993, pp 11–22.

These articles establish that those skilled in the art believe that in vitro screens are the primary method by which new antineoplastic compositions will be discovered. Progress has been sorely lacking in treating many kinds of cancer, as effective antineoplastic compositions for these cancers have not been discovered. Plainly, the public interest is served by maximizing, within Constitutional limits, the rewards for discovering a composition which is demonstrated to be effective in standard screening tests.

The Constitution of the United States (Art. 1, Sec. 8) authorizes Congress to establish the United States Patent and Trademark Office (USPTO) to promote scientific advancement. This obligation can only be fully met when the USPTO accepts current medical and scientific realities in the area of medical research.

The Framers of the Constitution meant to advance scientific advancement. Cells are alive. The impairment of human tumor cell growth is utility. The sole right obtained from the grant of Letters Patent is the right to prevent others from exploiting the subject matter of the patent. The recognition of cell line data as a measure of antineoplastic activity and therefore an acceptable showing of "utility" can aid research in the United States, and thereby save the citizens of the United States from being held hostage by foreign governments or foreign corporations, if such research is no longer viable in the United States.

Numerous compounds have been discovered which demonstrate significant antineoplastic activity. As discussed above, many of these compounds have been extracted, albeit with great difficulty, from living creatures such as the sponge or the sea hare. However, once the isolation and testing of such compounds has progressed, a practical problem exists, namely, how to obtain a significant quantity of the compound.

A major component of vigorous efforts for over two decades has been directed at marine sponge antineoplastic and/or cytotoxic biosynthetic products and it is toward the furtherance of that effort that the present invention is directed.

BRIEF SUMMARY OF THE INVENTION

Marine animal constituents of the macrocyclic lactone type, are proving to be exceptionally important sources of new anticancer drug candidates. Illustrative are current human clinical trials of bryostatin 1 and the advancing preclinical development of halichondrin B, halistatin 1 and ecteinascidin 729. Seven interesting (and cytotoxic) perhydropyrans of the onnamide series (from a Theonella species of marine sponge) and 13-deoxytedanolide, a cytotoxic macrocyclic lactone, from *Mycale adhaerens* (Porifera) are descriptive of related advances.

Spongistatin 1, described in applicant's co-pending application Ser. No. 08/006,279 was discovered in an Indian Ocean *Spongia sp* (family Spongiidae, class Demospongiae) and represents one of the most extraordinarily potent substances presently known against a subset of highly chemoresistant tumor types in the U.S. National Cancer Institute (NCI) panel of 60 human cancer cell lines. Intensive investigation of other active (P388 lymphocytic leukemia cell line bioassay) fractions from the same sponge species has revealed the presence of two new and exceptionally potent (NCI panel) macrocyclic lactones designated spongistatin 2 and 3.

Additionally, the typically bright colored (reds, purples) marine sponges of the genus Spirastrella (Class Demospongiae, Order Hadromerida, Family Spirastrellidae) have not heretofore been examined for biologically active constituents except for the arsenic content of *S. insignis*. In 1973 a 20 year investigation of antineoplastic constituents in *Spirastrella spinispirulifera* collected off the Southeast Coast of Africa was begun. The isolation and structure of remarkably potent antineoplastic substances from this sponge designated spongistatin 5, spongistatin 7, spongistatin 8 and spongistatin 9 is disclosed. Because these spongistatins prove to be only trace ($10^{-7}$% yield) constituents, their isolation and structural elucidation was especially difficult and protracted.

Accordingly, the principal object of the present invention is the isolation of structurally unprecedented macrocyclic lactones herein denominated spongistatin 5 and spongistatin 7; having a negative log molar $TGI_{50}$ of approximately ten against various human cancer cell lines, and the isolation of closely related compounds spongistatin 8 and spongistatin 9.

Another object of the present invention is to obtain the structural elucidation of the substance herein denominated spongistatin 5, spongistatin 7, spongistatin 8 and spongistatin 9.

A further object of the present invention is to determine a method of treating human cells afflicted with an NCI cell line human cancer, with spongistatin 5, spongistatin 7, spongistatin 8 and spongistatin 9.

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

Introduction

The present invention relates new macrocyclic lactones denominated spongistatin 5 and spongistatin 7 which are found to have remarkably potent and specific properties when tested against the NCI panel of human cancer cell lines and the related compounds spongistatin 8 and spongistatin 9. The structural formulas of these compounds are as follows.

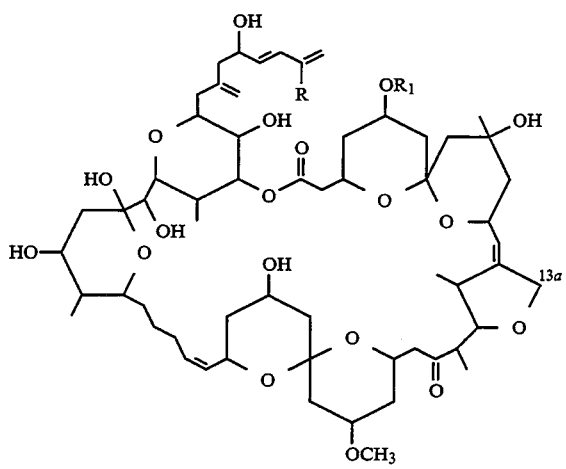

2a, R = Cl, $R_1$ = H     Spongistatin 5
b, R = H, $R_1$ = H     Spongistatin 7
c, R = H, $R_1$ = $COCH_3$     Spongistatin 8
d, R = Cl, $R_1$ = $COCH_3$     Spongistatin 9

Isolation of Spongistatins 5, 7, 8 and 9

In July, 1980, a large scale recollection (2,409 kg) of *Spirastrella spinispirulifera* preserved in ethanol was completed. The initial extraction, solvent partitioning and preparative HPLC was done on a pilot plant scale.

Separation Scheme Part 1 outlines the process whereby sponge material was extracted with 2-propanol, the resulting extract was concentrated, then diluted with water and extracted with methylene chloride. The dried methylene chloride extract (13.86 kg) was next partitioned with hexane and methanol-water (9:1) and the aqueous methanol then taken to dryness (2 kg). The final pilot plant scale high performance liquid chromatography (HPLC) separation (SILICA GEL, 0.15×3 m column at 150 psi) was carried out using the following-step wise gradient system: methylene chloride-methanol, 100-0 (160 1), 96-4 (205 1) 94-6 (102 1), 93-7 (102 1), 90-10 (102 1), 85-15 (102 1) and 80-20 (110 1). The effluent was collected in 19 liter containers, examined by tlc and like fractions combined and concentrated. The resulting series of active fractions A–F (P388 $ED_{50}$ 0.2 to <0.01 μg/ml) were next subjected to chromatography on SEPHADEX LH-20 in methanol (10×130 cm columns) which gave new active fractions G–J (P388 $ED_{50}$ 0.02 to <$10^{-2}$ μg/ml).

Fraction G was applied to the first of three MERCK LOBAR size B SILICA GEL columns (25×310 mm) connected in series. A gradient of acetone-hexane (3:47) to acetone-hexane (2:3) was followed by a gradient of methylene chloride-methanol (93:7) to methanol to give active fractions K–O (P388 $ED_{50}$ 1.8×$10^{-5}$ to <$10^{-5}$ μg/ml), as shown in Separation Scheme Part 2. Fraction K (38.9 mg) was then applied to two ANALTECH analytical tlc plates, 10×20 cm. Elution with acetone-hexane (1:1) provided a fraction enriched in a single component, K860 (3.6 mg). A second tlc separation was done, using 3.6 mg on an ANALTECH analytical plate (7.5×10 cm) with acetone-hexane, 3:2. A 0.3 mg amount of K860 resulted. From the earlier active fractions H, additional nearly pure K860 was isolated, 6.3 mg, which was combined with the 0.3 mg to give 6.6 mg total.

Further purification using HPLC (ALTEX Programmable Model 420 system, 2 model 110A pumps) with solvent gradient of $CH_2Cl_2$ to 93:7 $CH_2Cl_2$-MeOH on a PARTISIL M9 SILICA GEL column gave 6.3 mg of nearly pure K860. The sample was next chromatographed using HPLC (PARTISIL M9 10/50 ODS-2 column) with a methanol-$H_2O$ (1:1) to methanol gradient to give pure K860, spongistatin 4 (1.4 mg). A parallel separation sequence beginning with combined fractions M, N and O (42.0 mg) led to impure K859 (8.4 mg) which was purified by HPLC to give pure K859, spongistatin 7 (0.5 mg).

Active fraction I (Separation Scheme Part 3) was separated on SILICA GEL RP-2 (3.7×44 cm column) using the gradients, water to methanol, methanol to methylene chloride, to give active fraction P (1.75 g). Using the solvent system hexane-toluene-methanol (3:1:1) on SEPHADEX LH-20 (5.5×96 cm column) provided active fractions Q through U. Subjecting fraction U (0.173 g) to repetitive separations with a GILSON preparative system (Models 303 and 305 pump and PREPEX C8, 10×250 mm column) with the isocratic solvent, 36% acetonitrile in water and 1.2–1.8 mg/injection, gave fraction V (42.1 mg) containing spongistatins 4 and 5 and fraction W (29.2 mg) containing spongistatins 6 and 7. Final separation was achieved by repetitive analytical (GILSON) HPLC separations on LI-CHROSPHER 100 RP18 (4.6×250 mm), 45% acetonitrile in water and 0.2–0.3 mg per injection. The detection of HPLC peaks was by UV, λ=230 mm.

Active fractions S and T were combined (111.0 mg) and subjected to chromatography on SEPHADEX LH-20 (2.5×72 cm column) using hexane-toluene-methanol, 2:2:1. Resulting active fraction X (35.5 mg) was separated on HPLC (GILSON, preparative, PREPEX C8, 10×250 mm) using 36% acetonitrile in water and 1.2–1.8 mg/injection. Active fraction Y contained impure spongistatin 8 (3.95 mg) and active fraction Z yielded 8.15 mg of impure spongistatin 9. Final HPLC separation (Separation Scheme Part 4) resulted in pure spongistatin 8 (1.8 mg) and spongistatin 9 (5.4 mg).

The above described scheme afforded 12.9 mg (5.4×$10^{-7}$%, PS $ED_{50}$ 6.6×$10^{-5}$ μg/ml) of spongistatin 5; mp 186°–187° C.; $[\alpha]^{22}_D = -11.1°$ (c=0.23, $CH_3OH$); UV ($CH_3OH$) $\lambda_{max}$ 228 nm, ε 14840; IR (film) 3430, 2936, 1734, 1643, 1591, 1387, 1273, 1173, 1090, 982 $cm^{-1}$; high resolution FABMS, m/z 1175.5239 $[M+K]^+$ corresponding to $C_{59}H_{89}ClO_{19}K$ (calcd mass 1175.5324); 5.3 mg (2.2×$10^{-7}$% yield) of spongistatin 7; P388 $ED_{50}$ 2.6×$10^{-3}$; mp 166°–167° C.; $[\alpha]_D^{22}$ −15.7° (c, 0.15, $CH_3OH$); UV ($CH_3OH$) $\lambda_{max}$ 223 nm (log ε 4.25); IR (film) 3428, 2936, 1736, 1603, 1389, 1273, 1173, 1090, 984 $cm^{-1}$; HRFAB MS m/z 1141.5658 $[M+K]^+$, calcd for $C_{59}H_{90}O_{19}K$ 1141.5653; 1.8 MG (7.5×$10^{-8}$%, PS $ED_{50}$ 8×$10^{-4}$ μg/ml) of colorless spongistatin 8; mp 158°–159° C.; $[\alpha]_D^{22}$ −32° (c, 0.18, $CH_3OH$); IR(film) 3439, 2936, 1736, 1653, 1602, 1383, 1252, 1178, 1090 $cm^{-1}$; 5.4 mg (2.2×$10^{-7}$% yield, PS $ED_{50}$ <$10^{-4}$ μg/ml) of spongistatin 9; mp 164°–165°; $[\alpha]_D^{22}$ −33.3° (C, 0.14, $CH_3OH$); IR (film) 3435, 2940, 1736, 1647, 1591, 1385, 1254, 1178, 1090 $cm^{-1}$.

Once the structure of spongistatin 1 was established and its relationship to spongistatins 5, 7, 8 and 9 determined, structure solutions for the Spirastrella antineoplastic constituents were conducted as will be later described.

Superficially the $^{13}C$- and $^1H$-NMR spectra of spongistatin 5 was similar to those of spongistatins suggesting a similar skeleton. The four methyl doublet signals at δ 1.01 (J=6.7 Hz), 1.14 (J=7.0 Hz), 0.90 (J=7.1 Hz), and 0.85 (J=6.7 Hz), one methyl singlet at δ 1.14, one methoxyl signal at δ 3.31 and the $SP^2$ proton signals at δ 5.38 (doublet of doublets, J=10,11 Hz), 5.47 (doublet of triplets, J=7,11 Hz), 4.97 (broad singlet), 4.95 (broad singlet), 6.13 (broad doublet of doublets, J=6,15 Hz), 6.41 (broad doublet, J=15 Hz), 5.42 (broad singlet) and 5.33 (broad singlet) were consistent with this assumption. Furthermore, the coupling pattern of the signals at δ 5.42, 5.33 and 6.41 and the lack of an H-50 signal suggested a chlorine atom at C-50. But further analyses of 1D and 2D NMR spectra revealed significant difference between spongistatin 5 and spongistatins 1–4 and 6 in two respects: first, the absence of an acetyl signal; second, the pair of $SP^2$ methylene signals for H-13a common to spongistatins 1–4 were not present. In a $^1H$-$^{13}C$ correlated spectrum, a $^{13}C$ signal at δ 70.72 was found correlated with two $^1H$ signals at δ 4.47 (broad doublet, J=13 Hz) and 4.09 (broad doublet, J=13 Hz). The $^1H$-$^1H$ COSY spectrum of spongistatin 5 displayed two signals at δ 4.47 and 4.09 with long range couplings to a signal at δ 5.24 (broad doublet, J=11 Hz). In turn, the signal at δ 5.24 was found coupled with a signal at δ 5.28 (broad doublet of doublets, J=9,11 Hz). In the $^{13}C$ NMR spectrum of spongistatin 5, signals for $SP^2$ carbon atoms at C-13, C-28, C-29, C-45, C-45a, C-48, C-49, C-50, C-51 were observed with chemical shifts essentially the same as found for spongistatins 1, 3 and 4. The remaining one $SP^2$ carbon signal at δ 120.13 showed a correlation only with the one proton signal at δ 5.24 in the ¹H-¹³C spectrum. Such evidence indicated that a C-12,13 double bond allylic to a C-13a atom bonded to oxygen that resulted in the AB pattern at δ 4.47 and 4.09 in the ¹H NMR spectrum was present in spongistatin 5. The dramatic downfield shift of the C-15 signal at δ 84.46 (δ 73.75 in spongistatin 4) suggested that a tetrahydrofuran ring comprising C-15, C-14, C-13 and C-13a was present. The molecular formula suggested by FABMS also favored this conclusion. The presence of a tetrahydrofuran ring was further confirmed by an HMBC spectrum in which the ¹³C signal at δ 84.46 ppm (C-15) was strongly correlated with one of the two H-13a signals at δ 4.47. All of the ¹H- and ¹³C-NMR data as well as the HMBC correlations strongly supported the structure assigned to spongistatin 5.

The structures assigned spongistatins 1–5 required extensive high field (400 and 500 MHz) 2-D NMR and high resolution mass spectral interpretations that were quite difficult. But, results of those challenging analyses proved very important to completing the structural elucidation of spongistatins 6 and 7. The ¹H-NMR spectrum of spongistatin 6 indicated a spongistatin-type ring system. For example, the four methyl signals present in spongistatins 1–5 were found at δ 0.97 (d, J=6.8 Hz), 1.12 (d, J=7.1 Hz), 0.91 (d, J=7.1 Hz), and 0.83 (d, J=6.6 Hz). The ¹H signals at δ 2.90 (broad d, J=18 Hz), 2.83 and a ¹³C signal at δ 215.29 were characteristic of the spongipyran C-17 carbonyl system. The presence of an ABX spin system at δ 5.04 (broad d, J=11 Hz), 5.17 (broad d, J=17 Hz), 6.33 (d,d,d, J=11,11,17 Hz) suggested a proton rather than a chlorine atom at C-50 similar to that of spongistatin 2. The presence of one acetyl group was evident by ¹H and ¹³C signals at δ 2.03 (s, 3H) 172.80, and 21.65. The ¹H-¹H COSY and ¹H-¹³C COSY experiments established the ¹H and ¹³C assignments. The chemical shifts of the H-5 and H-15 signals at δ 5.03 (1H, broad s) and 3.83 (1H, broad d, J=9 Hz) readily pointed to attachment of the acetyl group at C-5.

Analogous structural determination approaches were applied to spongistatin 7. The HRFAB MS data established molecular formula C₅₉H₉₀O₁₉ employing peak matching at m/z 1141.6 [M+K]+. Results of the 2D ¹H- and ¹³C- NMR experiments with spongistatin 7 again suggested a spongipyran ring system, but with the additional tetrahydrofuran ring found in spongistatin 5. The latter feature was revealed by the ¹H-¹³C signals at δ 5.29 (broad d,d, J=10,11 Hz)/67.26, 5.24 (broad d, J=10 Hz)/120.16, 4.48 (broad d, J=13 Hz), 4.10 (broad d, J=13 Hz)/70.75, and the signals at δ 3.92 (d,d, J=3.7, 10 Hz)/84.50. The presence of ABX signals at δ 5.04 (broad d, J=10 Hz), 5.17 (broad d, J=17 Hz), and 6.32 (d,d,d, J=10, 10, 17 Hz) were readily attributed to a hydrogen at C-50 rather than a chlorine atom. The tetrahydrofuran ring was confirmed by HMBC experiments when one of the two H-13a signals at δ 4.48 showed a cross peak with the C-15 signal at δ 84.50. The HR FABMS spectral data also strongly supported a spongipyran ring system bearing an additional tetrahydrofuran ring. Thus, the structure of spongistatin 7 was unambiguously established.

Due to the paucity of spongistatin 8 structural elucidation was simplified by first deducing the structure of spongistatin 9. Once those high resolution FABMS and high field 2D NMR interpretations were in hand for spongistatin 9, the structure of spongistatin 8 was completed as follows. The tetrahydrofuran ring of spongistatin 8 was recognized by chemical shifts at δ 4.45 (broad d, J-13 Hz), 4.10 (broad d, J-13 H)/70.70 and 1.95 (acetyl, s, 3H)/21.31 and 172.56 (acetyl, s, 3H). A signal at δ 6.33 (d,d,d, J-10,10,17 Hz) indicated that C-50 was devoid of the usual spongistatin chlorine atom at that position. A series of ¹H-¹H NMR COSY experiments allowed assignment of the remaining ¹H signals and the ¹³C NMR signals were interpretated by comparison with the analogous NMR carbon data from spongistatin 9.

The structure of the spongistatin 9 was determined mainly by high field NMR spectroscopy utilizing results of ¹H-¹H COSY, ¹H-¹³C COSY, APT, and HMBC NMR experiments. Both the ¹H- and the ¹³C-NMR spectra of spongistatin 9 indicated that it was a member of the spongistatins by signals at δ 1.13 (3H, S)/30.17, 1.04 (3H, d)/14.59, 1.14 (3H, d)/15.10, 0.89 (3H, d)/11.52, 0.84 (3H, d)/13.00 an ester carbonyl signal at δ 173.66 and a ketone carbonyl signal at δ 213.42. Spongistatin 9 was found to possess a tetrahydrofuran ring by signals at δ 4.45 (broad doublet, J-13 Hz) and 4.10 broad doublet, J-13 Hz) corresponding to two H-13a. An acetyl group was evident by signals at δ 1.95 (3H)/21.35 and 172.61. That the acetyl group was attached to C-5 oxygen atom was evidenced by the chemical shift of H-5 at δ 4.96. The two broad singlets at δ 5.42 and 5.33 and the lack of a ¹H signal for C-50 were indicative of a chlorine atom at that position. Complete assignment for the ¹H- and ¹³C-NMR signals appear in Compilation 1 together with the APT and HMBC results.

Compilation 1.
Preparative HPLC of *Spirastrella spinispirulifera* Extract

| Column | Fractions* | | Amount Concentrate (g) | P388 ED₅₀ (μg/ml) |
|---|---|---|---|---|
| One: 2.0 Kg initial weight | 1–4 | | 1700 rechromatographed on 2nd column | — |
| | 5–15 | | 0.0 | — |
| | 16–17 | | 12.5 | 17.0 |
| | 18–19 | | 9.0 | 2.3 |
| | 20–21 | A | 16.0 | 0.2 |
| | 22–27 | B | 28.0 | 0.13 |
| | 28–35 | | 11.0 | 1.5 |
| | 36–47 | | 45.0 | 1.4 |
| | 48–51 | | 28.0 | 10.0 |
| Two: 1.7 Kg initial weight | precipitate, batyl alcohol | | 145.0 | — |
| | 1–2 | | 0.0 | — |
| | 3–9 | | 470.0 | 17.0 |
| | 10–11 | | 150.0 | 1.2 |
| | 12–14 | | 140.0 | 11.0 |
| | 15–18 | C | 275.0 | 0.14 |
| | 19–26 | D | 100.0 | <0.01 |
| | 27–34 | E | 35.0 | 0.21 |
| | 35–46+ | F | 175.0 | 0.30 |

Visualization took place with both uv and spray reagents of 5% ceric sulfate in 15% sulfuric acid and 1:2:97 anisaldehyde-sulfuric acid-acetic acid.
*Fraction volume was 19 liter each, and like fractions were combined and concentrated by tlc comparisons. Tlc system was 95:5 methylene chloride-methanol on Brinkman Sil G/UV 254 20 × 20 cm plates with batyl alcohol used as a reference sample.

Separation Scheme Part 1

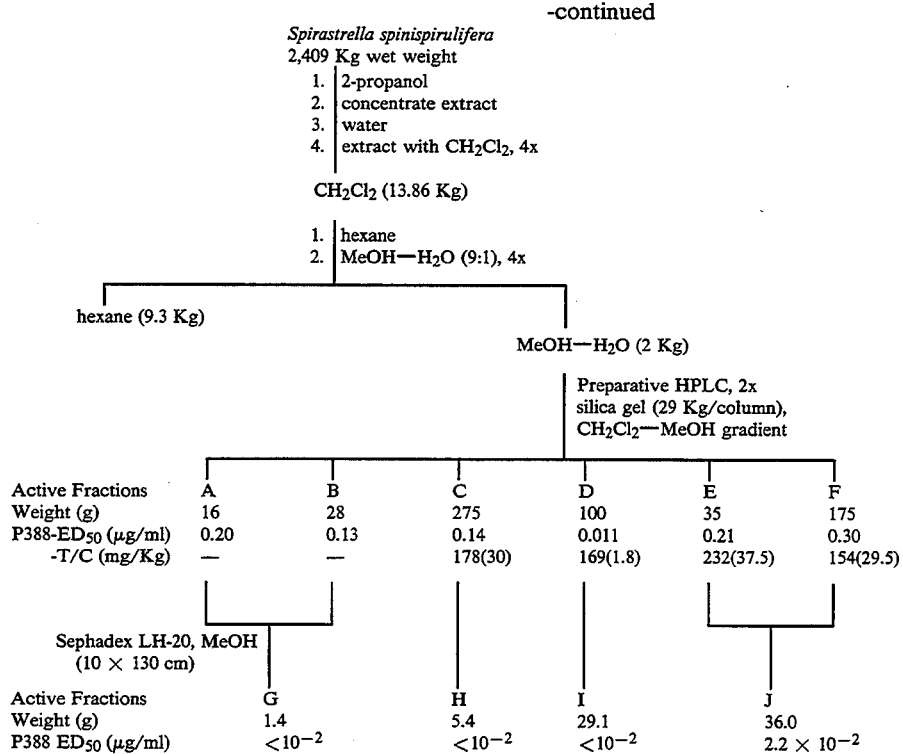
Separation Scheme Part 2
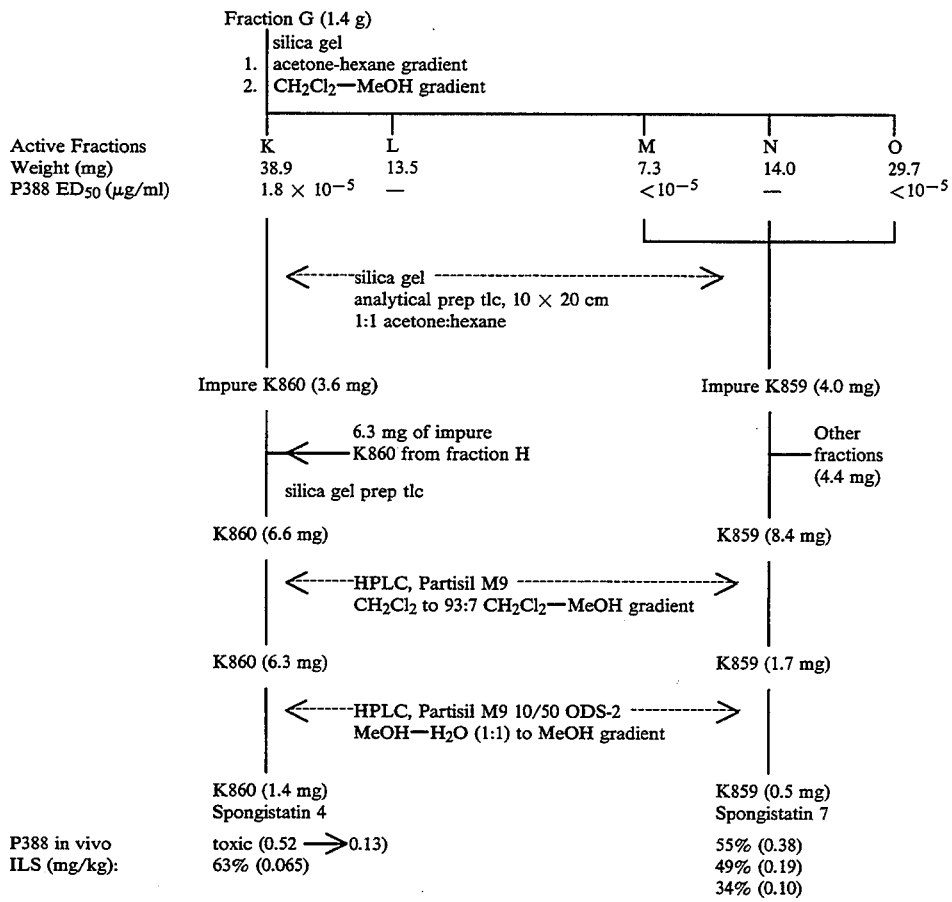
Separation Scheme Part 3

-continued

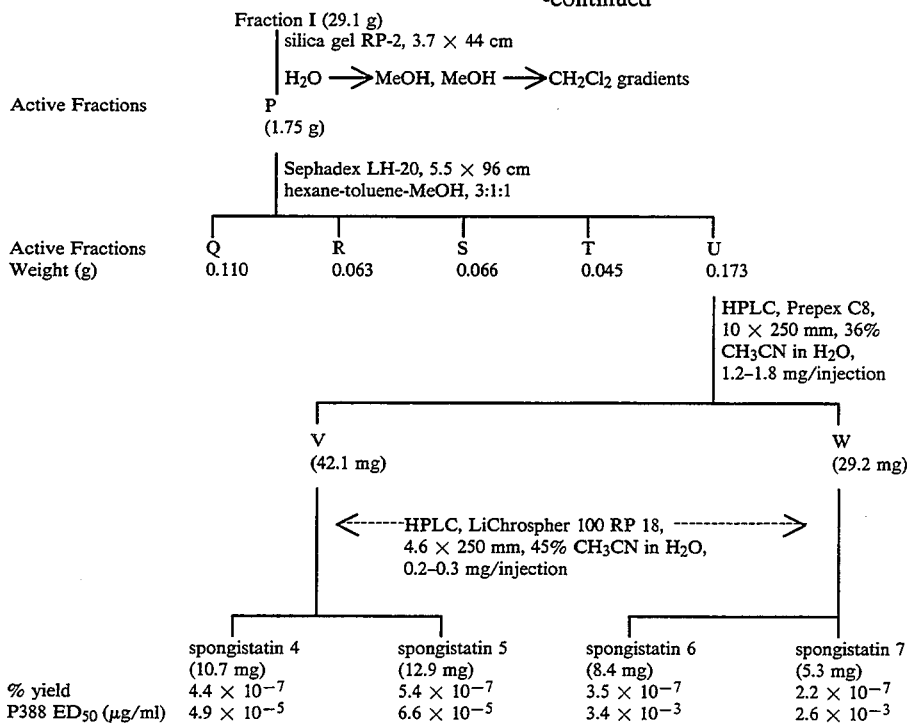

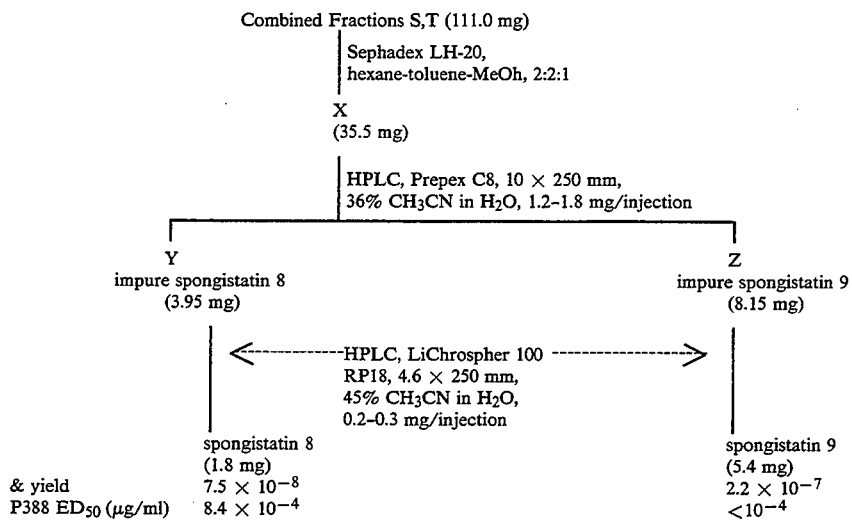

Evaluation of spongistatin 5 and spongistatin 7 against the U.S. National Cancer Institute panel of 60 human cancer cell lines gave dramatic results. Comparative testing of spongistatin 5 and spongistatin 7 in the NCI 60 cell line in vitro screening panel revealed an overall potency of spongistatin 5 and spongistatin 7 comparable to spongistatin 1 (e.g., panel mean $GI_{50}$ $10^{-10}$M; Table 1). The compounds are among the most potent of all substances tested to date in the NCI screen. Interestingly, several of the human breast cancer cell lines recently incorporated into the NCI screening panel were among the most sensitive (e.g., $GI_{50}$ $10^{-11}$–$10^{-12}$M). Furthermore, results of pattern-recognition analyses revealed that the highly distinctive mean-graph "fingerprint" (pattern of relative cellular sensitivity) produced in common by spongistatins 1, 5 and 7 (Table 1) is closely correlated in turn (data not shown) with that shared by the important general class of microtubule-interactive antimitotics. The structural variations thus far observed in this intriguing new family of antineoplastic substances do not result in substantial loss of the critical in vitro activity attributes. Animal data demonstrated an increased life span (ILS) of 78% at 10 μg/kg dose for spongistatin 1, an ILS of 65% at 5 μg/kg dose for spongistatin 5 and an ILS of 60% at 40 μg/kg for spongistatin 7. The advantageous or disadvantageous effects of these structural variations upon the in vivo activity potential is unknown, but will be addressed in further biological evaluations of all of the available compounds so remarkably active in vitro.

Discovery of the spongistatins in quite distant (in respect to taxonomy and geography) Porifera species suggests that this very important new series of remarkable antineoplastic agents may prove to be widely distributed in such marine invertebrates and/or associated marine microorganisms. Interestingly, a recent first-study of Porifera found adjoining Easter Island, the most remote South Pacific Island, uncovered both *Spirastrella cunctatrix* and *Spongia virgultosa* in the same general area. A future examination of these two sponges for spongistatins should prove useful. Presently extended in vivo human cancer xenograft evaluations of spongistatins 4 and 5 are being pursued. Also research directed at completing the absolute configurational assignments for the spongistatins by X-ray crystal structure determinations is underway. The NMR data for spongistatin 5, spongistatin 7, spongistatin 8 and spongistatin 9 appear on Tables 2, 3, 4 and 5. The currently available in vivo data for spongistatins 1, 4, 5, 6 and 7 appears in Table 6. NCI cell line data for spongistatins 5 and 7 appear in Tables 7 and 8.

TABLE 1

Results of Comparative Antitumor Evaluations of Spongistatins 1, 5 and 7 in the NCI In Vitro Primary Screen[a]

| Spongistatin Number | Mean Panel $GI_{50}$ ($\times 10^{-10}$ M)[b] | Compare Correlation Coefficient[c] |
|---|---|---|
| 1 | 1.17 | 1.00 |
| 5 | 1.23 | 0.92 |
| 7 | 10.10 | 0.81 |

[a]All compounds were tested in quadruplicate at five different concentrations ($10^{-8}$, $10^{-9}$, $10^{-10}$, $11^{-11}$ and $10^{-12}$ M) against the entire panel of 60 human tumor cell lines comprising the NCI screen.
[b]Standard errors averaged less than 15% of the respective means.
[c]Correlation coefficients from the Compare pattern-recognition algorithm were calculated by computer using the TGI-centered mean graph profiles of differential cellular sensitivities to 1, and 5. The TGI mean graph profile of 1 was used as the benchmark or "seed" for all of the comparisons.

TABLE 2

NMR Assignments for Spongistatin 5 Recorded in $CD_3OD$, the coupling constants are in Hz (in parenthesis); the n and p are APT results.

| | $^{13}C$(100 MHz) | $^{1}H$(400 MHz) | HMBC(500 MHz, C to H) |
|---|---|---|---|
| 1 | 173.80p | | H-2,H-41 |
| 2 | 40.15p | 2.70 *,2.70 * | |
| 3 | 63.28n | 4.56 brm | H-2,H-4 |
| 4 | 37.92p | 1.78 *;1.63 * | H-6 |
| 5 | 65.54n | 4.07 brs | H-6 |
| 6 | 40.62p | 1.86 *;1.74 * | H-8 |
| 7 | 101.49p | | H-8,H-5,H-6 |
| 8 | 45.99p | 1.74 *;1.58 * | H-9a,H-10 |
| 9 | 69.46p | | H-9a,H-8 |
| 9a | 30.05n | 1.14 s | H-10 |
| 10 | 45.01p | 1.57 *;1.48 dd(11,12) | H-9a,H-8 |
| 11 | 67.23n | 5.28 brdd(9,11) | H-10 |
| 12 | 120.13n | 5.24 brd(11) | H-13a,H-10 |
| 13 | 148.64p | | H-14a,H-13a |
| 13a | 70.72p | 4.47 brd(13); 4.09 brd(13) | H-12,H-14 |
| 14 | 37.82n | 3.29 brm | H-14a,H-12,H-16 |
| 14a | 15.09n | 1.01 d(6.7) | H-15 |
| 15 | 84.46n | 3.92 dd(3.7,10) | H-16a,H-14a,H-13a, H-16 |
| 16 | 47.03n | 2.86 dq(7,11) | H-16a |
| 16a | 14.56n | 1.14 d(7.0) | H-16 |
| 17 | 213.24p | | H-16a,H-18,H-15 |
| 18 | 50.99p | 2.95 dd(10,19), 2.82 brd(19) | |
| 19 | 66.79n | 4.14 brt(11) | H-18,H-20 |
| 20 | 38.06p | 2.07 *;1.03 * | H-22 |
| 21 | 74.60n | 3.58 m | H-20,H—OMe,H-22 |
| 22 | 44.14p | 2.05 *; 1.18 ddd(12,12,12) | |
| 23 | 100.17p | | H-22,H-24 |

TABLE 2-continued

NMR Assignments for Spongistatin 5 Recorded in $CD_3OD$, the coupling constants are in Hz (in parenthesis); the n and p are APT results.

| | $^{13}C$(100 MHz) | $^{1}H$(400 MHz) | HMBC(500 MHz, C to H) |
|---|---|---|---|
| 24 | 34.77p | 2.40 brd(14);1.63 * | H-22 |
| 25 | 65.12n | 4.02 brs | H-24 |
| 26 | 39.14p | 1.62 *;1.62 * | H-24 |
| 27 | 61.91n | 5.04 ddd(5,9,10) | H-29 |
| 28 | 131.26n | 5.38 dd(10,11)) | H-30 |
| 29 | 134.05n | 5.47 dt(7,11) | H-30 |
| 30 | 28.30p | 2.13 *;2.13 * | H-28 |
| 31 | 27.42p | 1.65 *;1.25 * | H-30 |
| 32 | 33.21p | 1.46 *;1.30 * | H-30 |
| 33 | 67.99n | 4.21 brd(9) | H-34a,H-35 |
| 34 | 39.57n | 1.62 * | H-34a,H-36 |
| 34a | 11.49n | 0.90 d(7.1) | H-34,H-33 |
| 35 | 72.03n | 3.75 * | H-34a,H-36,H-34 |
| 36 | 34.26p | 2.00 *;1.63 * | H-38 |
| 37 | 99.40p | | H-38,H-36,H-35 |
| 38 | 73.32n | 3.38 brs | |
| 39 | 81.76n | 3.76 * | H-40a,H-40 |
| 40 | 37.60n | 2.02 * | H-40a,H-41 |
| 40a | 13.00n | 0.85 d(6.7) | H-41,H-40 |
| 41 | 80.72n | 4.88 dd(9,11) | H-40a,H-42,H-39, H-40 |
| 42 | 73.81n | 3.18 t(9) | H-41,H-44 |
| 43 | 79.69n | 3.44 brt(11) | H-42,H-39,H-44 |
| 44 | 40.49p | 2.80 *;2.19 * | H-45a,H-46,H-42 |
| 45 | 143.83p | | H-44,H-46,H-47, H-45a,H-43 |
| 45a | 116.34n | 4.97 brs;4.95 brs | H-44,H-46 |
| 46 | 44.34p | 2.34 brdd(7.3,14), 2.25 brdd(6.1,14) | H-45a,H-44,H-47 |
| 47 | 71.03n | 4.38 ddd(6.5,6.5,6.5) | H-46,H-48,H-49 |
| 48 | 138.77n | 6.13 brdd(6,15) | H-46,H-47 |
| 49 | 127.87n | 6.41 brd(15) | H-51,H-47 |
| 50 | 139.61p | | H-48,H-49,H-51 |
| 51 | 116.16p | 5.42 brs 5.33 brs | H-49 |
| OMe | 55.87n | 3.31 s | H-21 |

* Coupling constants for these signals are not measured due to overlapping.

TABLE 3

NMR Assignments for spongistatin 7 in $CD_3OD$ (n and p are APT results, coupling constants are in Hz in parenthesis). The mixing time for the HMBC experiment was set at 130 micro second).

| | $^{13}C$(100 MHz) | $^{1}H$(400 MHz) | HMBC(500 MHz, C to H) |
|---|---|---|---|
| 1 | 173.83p | | H-41 |
| 2 | 40.17p | 2.69 *;2.69 * | |
| 3 | 63.30n | 4.56 brm | H-2,H-8 |
| 4 | 37.94p | 1.74 *;1.60 * | |
| 5 | 65.58n | 4.07 brs | H-6 |
| 6 | 40.66p | 1.87 brd(14);1.74 * | H-8 |
| 7 | 101.52p | | H-8,H-6 |
| 8 | 46.03p | 1.72 *;1.58 * | H-9a,H-6 |
| 9 | 69.47p | | H-9a,H-8 |
| 9a | 30.07n | 1.14 s | H-8 |
| 10 | 45.05p | 1.56 *;1.48 dd(11,14) | H-9a |
| 11 | 67.26n | 5.29 brdd(10,11) | H-10,H-6 |
| 12 | 120.16n | 5.24 brd(10) | H-13a,H-10 |
| 13 | 148.68p | | H-14a,H-13a,H-15, H-14 |
| 13a | 70.75p | 4.48 brd(13); 4.10 brd(13) | |
| 14 | 37.86n | 3.28 * | H-14a |
| 14a | 15.13n | 1.01 d(6.6) | H-15 |
| 15 | 84.50n | 3.92 dd(3.7,10) | H-16a,H-14a,H-13a, H-16 |
| 16 | 47.06n | 2.86 dq(7,10) | H-16a,H-15 |
| 16a | 14.57n | 1.14 d(7.0) | H-16,H-15 |
| 17 | 213.24p | | H-16a,H-18,H-15 |
| 18 | 51.02p | 2.95 dd(10,19), 2.82 brd(19) | |
| 19 | 66.82n | 4.14 * | |
| 20 | 38.10p | 2.07 *;1.03 * | H-22,H-18 |
| 21 | 74.63n | 3.59 m | H—OMe |
| 22 | 44.18p | 2.05 *;1.18 t(12) | H-24 |

TABLE 3-continued

NMR Assignments for spongistatin 7 in CD₃OD (n and p are APT results, coupling constants are in Hz in parenthesis). The mixing time for the HMBC experiment was set at 130 micro second).

| | $^{13}$C(100 MHz) | $^1$H(400 MHz) | HMBC(500 MHz, C to H) |
|---|---|---|---|
| 23 | 100.22p | | H-22,H-24 |
| 24 | 34.80p | 2.40 brd(14);1.62 * | H-22,H-25 |
| 25 | 65.15n | 4.02 brs | H-24,H-22 |
| 26 | 39.16p | 1.64 *;1.62 * | |
| 27 | 61.94n | 5.04 * | H-29 |
| 28 | 131.31n | 5.39 t(10) | |
| 29 | 134.10n | 5.46 dt(7,10) | |
| 30 | 28.31p | 2.13 *;2.13 * | H-29 |
| 31 | 27.40p | 1.65 *;1.25 * | H-29 |
| 32 | 33.28p | 1.45 *;1.29 * | |
| 33 | 68.02n | 4.21 brd(9) | H-34a,H-35 |
| 34 | 39.59n | 1.62 * | H-34a,H-35,H-36 |
| 34a | 11.51n | 0.90 d(7.2) | H-35 |
| 35 | 72.08n | 3.77 * | H-34a,H-36 |
| 36 | 34.28p | 2.02 *;1.66 * | H-38,H-35 |
| 37 | 99.45p | | H-38,H-36 |
| 38 | 73.35n | 3.38 brs | H-36 |
| 39 | 81.77n | 3.76 * | H-40a |
| 40 | 37.63n | 2.02 * | H-40a,H-41 |
| 40a | 13.03n | 0.85 d(6.5) | H-41 |
| 41 | 80.76n | 4.88 * | H-40a,H-42,H-39 |
| 42 | 73.83n | 3.18 t(9) | H-41,H-44 |
| 43 | 79.74n | 3.43 brt(9) | H-42,H-39,H-44 |
| 44 | 40.45p | 2.78 brd(14) *;2.17 * | H-46,H-42 |
| 45 | 144.01p | | H-44,H-46,H-47 |
| 45a | 116.08p | 4.94 brs;4.92 brs | H-44 |
| 46 | 44.45p | 2.34 brdd(7,14), 2.21 brdd(6.6,14) | H-48,H-44,H-47 |
| 47 | 71.65n | 4.27 q(6.5) | H-46,H-48,H-49 |
| 48 | 137.65n | 5.70 brdd(6.5,15) | H-46,H-47,H-50, H-51 |
| 49 | 132.01n | 6.23 brdd(10,15) | H-50,H-51,H-47 |
| 50 | 137.99n | 6.32 ddd(10,10,17) | H-51 |
| 51 | 117.46p | 5.17 brd(17) 5.04 brd(10) | H-49 |
| OMe | 55.90n | 3.31 s | H-21 |

* Coupling constants for these signals are not measured due to overlapping.

TABLE 4

NMR Assignments for Spongistatin 8 Recorded in CD₃OD. The coupling constants are in Hz (in parenthesis); the n and p are APT results; The mixing time for the HMBC was set at 130 microsecond.

| | $^{13}$C(100 MHz) | $^1$H(400 MHz) | HMBC(500 MHz, C to H) |
|---|---|---|---|
| 1 | 174.18p | | H-41 |
| 2 | 40.29p | 2.67 *;2.67 * | |
| 3 | 63.79n | 4.62 brm | H-2 |
| 4 | 35.13p | 1.82 brd(14);1.67 * | |
| 5 | 68.36n | 4.97 brs | |
| 6 | 37.73p | 2.11 *;1.68 * | |
| 7 | 99.96p | | H-8 |
| 8 | 46.27p | 1.71 *;1.50 d(14) * | H-9a |
| 9 | 69.78p | | H-9a |
| 9a | 30.13n | 1.14 s | |
| 10 | 44.92p | 1.55 brd(14); 1.40 dd(11,14) | H-9a |
| 11 | 66.41n | 5.15 * | |
| 12 | 120.74n | 5.20 * | |
| 13 | 148.05p | | H-14a |
| 13a | 70.70p | 4.45 brd(13); 4.10 brd(13) | |
| 14 | 37.79n | 3.31 * | H-14a |
| 14a | 14.54n | 1.04 d(6.7) | |
| 15 | 84.67n | 3.90 dd(3.8,10) | H-16a,H-14a |
| 16 | 47.00n | 2.87 * | H-16a |
| 16a | 15.07n | 1.15 d(7.3) | |
| 17 | 213.34p | | H-16a,H-18 |
| 18 | 51.05p | 2.95 dd(10,19), 2.83 brd(19) | |
| 19 | 66.78n | 4.14 * | |
| 20 | 38.08p | 2.07 *;1.04 * | |
| 21 | 74.60n | 3.59 m | H—OMe |
| 22 | 44.12p | 2.05 *;1.20 t(12) | |

TABLE 4-continued

NMR Assignments for Spongistatin 8 Recorded in CD₃OD. The coupling constants are in Hz (in parenthesis); the n and p are APT results; The mixing time for the HMBC was set at 130 microsecond.

| | $^{13}$C(100 MHz) | $^1$H(400 MHz) | HMBC(500 MHz, C to H) |
|---|---|---|---|
| 23 | 100.18p | | H-24 |
| 24 | 34.77p | 2.40 brd(14);1.63 * | |
| 25 | 65.12n | 4.02 brs | |
| 26 | 39.13p | 1.62 *;1.62 * | |
| 27 | 61.97n | 5.06 * | |
| 28 | 131.24n | 5.39 brt(10) | |
| 29 | 133.96n | 5.49 m | |
| 30 | 28.27p | 2.13 *;2.10 * | |
| 31 | 27.34p | 1.65 *;1.29 * | |
| 32 | 33.15p | 1.46 m;1.31 m | |
| 33 | 67.91n | 4.22 m | H-34a |
| 34 | 39.51n | 1.62 * | H-34a |
| 34a | 11.47n | 0.90 d(7.3) | |
| 35 | 72.05n | 3.77 brs | H-34a |
| 36 | 34.24p | 2.02 *;1.67 * | |
| 37 | 99.43p | | H-38,H-36 |
| 38 | 73.33n | 3.38 brs | |
| 39 | 81.70n | 3.75 * | H-40a |
| 40 | 37.67n | 2.03 * | H-40a |
| 40a | 12.95n | 0.84 d(6.5) | |
| 41 | 80.73n | 4.88 * | H-40a,H-42 |
| 42 | 73.76n | 3.18 t(9) | |
| 43 | 79.67n | 3.43 brdd(9,10) | H-42 |
| 44 | 40.47p | 2.78 brd(14); 2.16 brdd(10,14) | H-42 |
| 45 | 143.96p | | |
| 45a | 116.08p | 4.94 brs;4.92 brs | |
| 46 | 44.45p | 2.35 brdd(7,14), 2.21 brdd(7,14) | |
| 47 | 71.61n | 4.29 ddd(6,7,7) | |
| 48 | 137.61n | 5.71 brdd(6.7,15) | |
| 49 | 131.99n | 6.23 brdd(10,15) | |
| 50 | 137.97n | 6.33 ddd(10,10,17) | |
| 51 | 117.41p | 5.17 brd(17) 5.04 brd(10) | |
| OMe | 55.87n | 3.34 s | |
| OAc | 172.56p | | H—OAc |
| | 21.30n | 1.95 s | |

* Coupling constants for these signals are not measured due to overlapping.

TABLE 5

NMR Assignments for spongistatin 9 recorded in CD₃OD. The coupling constants are given by (Hz) and the n and p refer to APT results. The mixing time for the HMBC experiment was set at 60 microsecond.

| | $^{13}$C(100 MHz) | $^1$H(400 MHz) | HMBC(500 MHz, C to H) |
|---|---|---|---|
| 1 | 173.66p | | H-2,H-3,H-41 |
| 2 | 40.36p | 2.67 *;2.67 * | |
| 3 | 63.86n | 4.62 brm | H-2,H-4,H-8 |
| 4 | 35.18p | 1.82 brd(14);1.68 * | H-2,H-6 |
| 5 | 68.40n | 4.96 brs | H-6 |
| 6 | 37.82p | 2.11 *;1.67 * | H-8 |
| 7 | 100.00p | | H-8,H-6 |
| 8 | 46.32p | 1.71 *;1.50 d(14) * | H-9a,H-10 |
| 9 | 69.83p | | H-9a,H-8,H-10 |
| 9a | 30.17n | 1.13 s | H-8 |
| 10 | 44.97p | 1.55 brd(14); 1.40 dd(11,14) | H-9a,H-8 |
| 11 | 66.46n | 5.14 brdd(10,11) | H-10 |
| 12 | 120.78n | 5.19 brd(10) | H-13a,H-10 |
| 13 | 148.08p | | H-14a,H-13a |
| 13a | 70.74p | 4.45 brd(13); 4.10 brd(13) | H-12 |
| 14 | 38.12n | 3.31 * | H-14a,H-12 |
| 14a | 14.59n | 1.04 d(6.8) | |
| 15 | 84.73n | 3.90 dd(3.8,10) | H-16a,H-14a,H-13a, H-16 |
| 16 | 47.04n | 2.86 * | H-16a |
| 16a | 15.10n | 1.14 d* | H-16,H-15 |
| 17 | 213.42p | | H-16a,H-18 |
| 18 | 51.10p | 2.96 dd(10,19), 2.84 brd(19) | |

TABLE 5-continued

NMR Assignments for spongistatin 9 recorded in CD3OD. The coupling constants are given by (Hz) and the n and p refer to APT results. The mixing time for the HMBC experiment was set at 60 microsecond.

| | $^{13}$C(100 MHz) | $^{1}$H(400 MHz) | HMBC(500 MHz, C to H) |
|---|---|---|---|
| 19 | 66.83n | 4.14 * | H-18,H-20 |
| 20 | 38.12p | 2.07 *;1.04 * | H-22 |
| 21 | 74.65n | 3.60 m | H-20,H—OMe,H-22 |
| 22 | 44.16p | 2.06 *;1.20 t(12) | |
| 23 | 100.23p | | H-22 |
| 24 | 34.81p | 2.41 brd(14);1.63 * | H-22 |
| 25 | 65.17n | 4.02 brs | H-24 |
| 26 | 39.20p | 1.62 *;1.62 * | H-24 |
| 27 | 62.02n | 5.05 ddd(5,9,10) | H-29 |
| 28 | 131.27n | 5.38 brt(10) | H-27 |
| 29 | 133.98n | 5.49 m | H-27 |
| 30 | 28.34p | 2.13 *;2.10 * | H-28,H-29 |
| 31 | 27.43p | 1.65 *;1.27 * | |
| 32 | 33.22p | 1.46 m;1.31 m | |
| 33 | 67.96n | 4.21 m | H-34a |
| 34 | 39.56n | 1.62 * | H-34a,H-36,H-34 |
| 34a | 11.52n | 0.89 d(7.1) | |
| 35 | 72.09n | 3.76 * | H-34a,H-36 |
| 36 | 34.30p | 2.02 *;1.67 * | H-38 |
| 37 | 99.47p | | H-38,H-36,H-35 |
| 38 | 73.38n | 3.38 brs | |
| 39 | 81.76n | 3.76 * | H-40a,H-40 |
| 40 | 37.69p | 2.03 * | H-40a,H-41,H-38 |
| 40a | 13.00n | 0.84 d(6.7) | H-41,H-40 |
| 41 | 80.78n | 4.88 * | H-40a,H-42,H-39, H-40 |
| 42 | 73.82n | 3.19 t(9) | H-41 |
| 43 | 79.71n | 3.43 brdd(9,10) | H-42,H-39,H-44 |
| 44 | 40.51p | 2.80 brd(14); 2.18 brdd(10,14) | H-45a,H-46,H-42 |
| 45 | 143.85p | | H-44,H-46,H-47 |
| 45a | 116.43p | 4.96 brs;4.95 brs | H-44,H-46 |
| 46 | 44.43p | 2.36 brdd(7,14), 2.25 brdd(7,14) | H-45a,H-44,H-47, H-48 |
| 47 | 71.07n | 4.39 ddd(6,7,7) | H-46,H-48,H-49 |
| 48 | 138.79n | 6.14 brdd(6,15) | H-46,H-47 |
| 49 | 127.93n | 6.41 brd(15) | H-51,H-47 |
| 50 | 139.65p | | H-48,H-49,H-51 |
| 51 | 116.18p | 5.42 brs 5.33 brs | H-49 |
| OMe | 55.92n | 3.34 s | H-21 |
| OAc | 172.61p | | H—OAc |
| | 21.35n | 1.95 s | |

* Coupling constants for these signals are not provided due to overlapping.

TABLE 6

In vivo data for spongistatins 1, 4, 5, 6 and 7

| Compound | Dose (μg/kg/dose) | % ILS |
|---|---|---|
| spongistatin 1 | 40.0 | −10 (toxic) |
| | 25.0 | +33 |
| | 10.0 | +72 |
| spongistatin 4 | 5.0 | +55 |
| spongistatin 5 | 5.0 | +65 |
| spongistatin 6 | 40.0 | +70 |
| spongistatin 7 | 40.0 | +60 |

Tumor system: P388; implant: IP 1.0 E + 06 cells; host: CD2FL female mice; median day of death: 10; schedule: IP, Q1D × 9 (1); vehicle: 5% ETOH + distilled water; % ILS: % increase in life span over the controls.

TABLE 7.

Human Tumor Cell Line Evaluation of Spongistatin 5

National Cancer Institute Developmental Therapeutics Program
Mean Graphs
NSC: V 3502
Report Date: March 26, 1993
Units: Molar
SSPL: r   Exp. ID: Averaged
High Conc: 1.000E-07

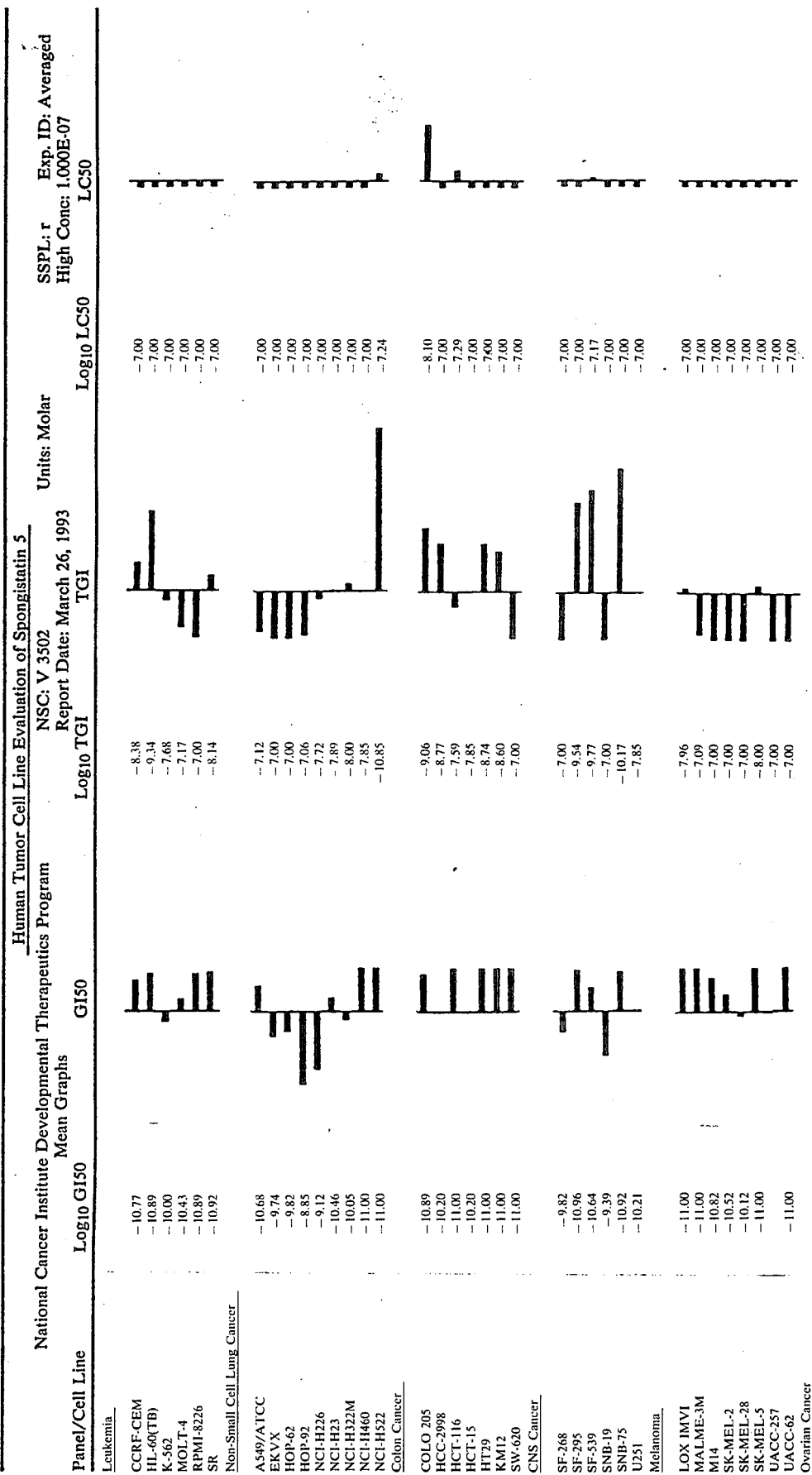

| Panel/Cell Line | Log10 GI50 | GI50 | Log10 TGI | TGI | Log10 LC50 | LC50 |
|---|---|---|---|---|---|---|
| Leukemia | | | | | | |
| CCRF-CEM | −10.77 | | −8.38 | | −7.00 | |
| HL-60(TB) | −10.89 | | −9.34 | | −7.00 | |
| K-562 | −10.00 | | −7.68 | | −7.00 | |
| MOLT-4 | −10.43 | | −7.17 | | −7.00 | |
| RPMI-8226 | −10.89 | | −7.00 | | −7.00 | |
| SR | −10.92 | | −8.14 | | −7.00 | |
| Non-Small Cell Lung Cancer | | | | | | |
| A549/ATCC | −10.68 | | −7.12 | | −7.00 | |
| EKVX | −9.74 | | −7.00 | | −7.00 | |
| HOP-62 | −9.82 | | −7.00 | | −7.00 | |
| HOP-92 | −8.85 | | −7.06 | | −7.00 | |
| NCI-H226 | −9.12 | | −7.72 | | −7.00 | |
| NCI-H23 | −10.46 | | −7.89 | | −7.00 | |
| NCI-H322M | −10.05 | | −8.00 | | −7.00 | |
| NCI-H460 | −11.00 | | −7.85 | | −7.00 | |
| NCI-H522 | −11.00 | | −10.85 | | −7.24 | |
| Colon Cancer | | | | | | |
| COLO 205 | −10.89 | | −9.06 | | −8.10 | |
| HCC-2998 | −10.20 | | −8.77 | | −7.00 | |
| HCT-116 | −11.00 | | −7.59 | | −7.29 | |
| HCT-15 | −10.20 | | −7.85 | | −7.00 | |
| HT29 | −11.00 | | −8.74 | | −7.00 | |
| KM12 | −11.00 | | −8.60 | | −7.00 | |
| SW-620 | −11.00 | | −7.00 | | −7.00 | |
| CNS Cancer | | | | | | |
| SF-268 | −9.82 | | −7.00 | | −7.00 | |
| SF-295 | −10.96 | | −9.54 | | −7.00 | |
| SF-539 | −10.64 | | −9.77 | | −7.17 | |
| SNB-19 | −9.39 | | −7.00 | | −7.00 | |
| SNB-75 | −10.92 | | −10.17 | | −7.00 | |
| U251 | −10.21 | | −7.85 | | −7.00 | |
| Melanoma | | | | | | |
| LOX IMVI | −11.00 | | −7.96 | | −7.00 | |
| MALME-3M | −11.00 | | −7.09 | | −7.00 | |
| M14 | −10.82 | | −7.00 | | −7.00 | |
| SK-MEL-2 | −10.52 | | −7.00 | | −7.00 | |
| SK-MEL-28 | −10.12 | | −7.00 | | −7.00 | |
| SK-MEL-5 | −11.00 | | −8.00 | | −7.00 | |
| UACC-257 | | | −7.00 | | −7.00 | |
| UACC-62 | −11.00 | | −7.00 | | −7.00 | |
| Ovarian Cancer | | | | | | |

TABLE 7-continued

Human Tumor Cell Line Evaluation of Spongistatin 5
National Cancer Institute Developmental Therapeutics Program
Mean Graphs
NSC: V 3502
Report Date: March 26, 1993
Units: Molar
SSPL: r    Exp. ID: Averaged
High Conc: 1.000E-07

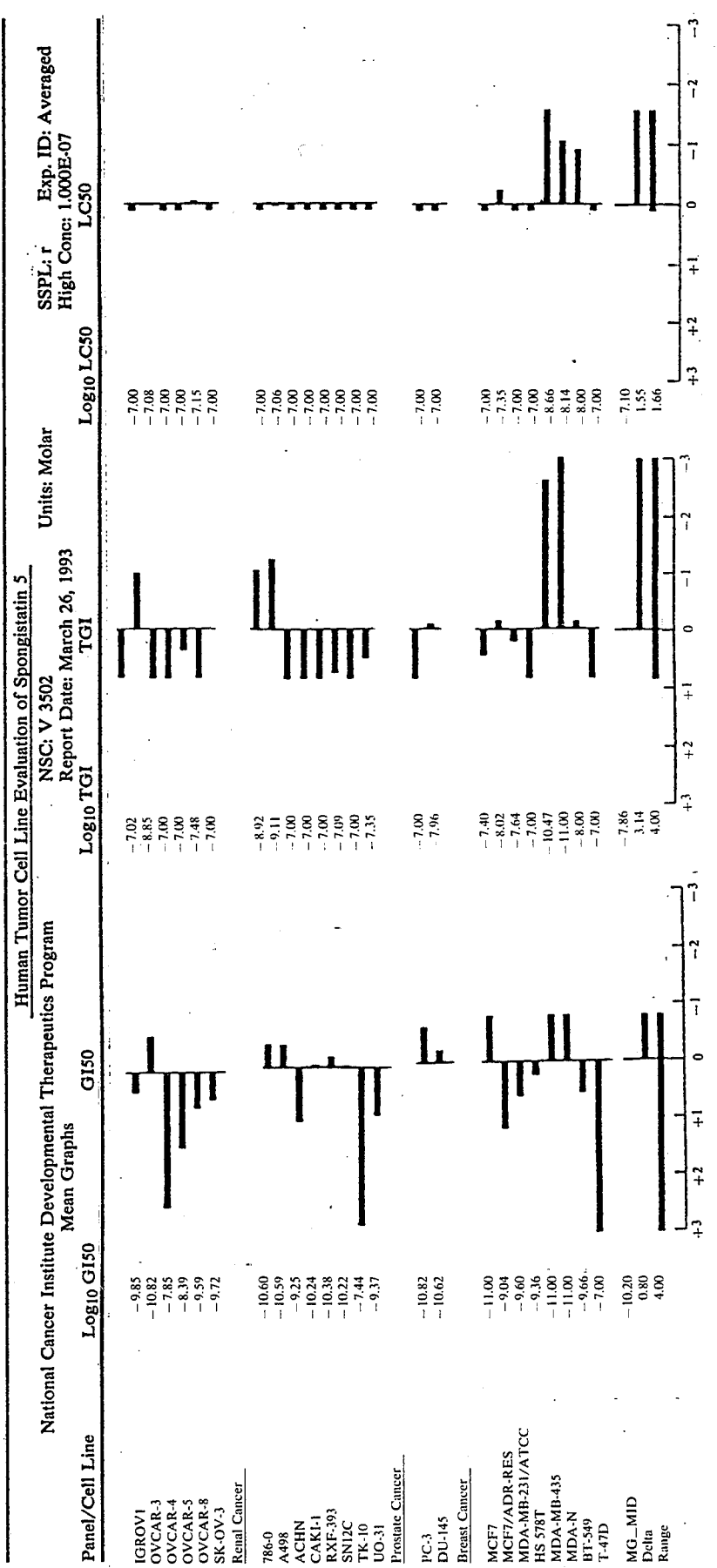

| Panel/Cell Line | Log₁₀ GI50 | Log₁₀ TGI | Log₁₀ LC50 |
|---|---|---|---|
| IGROV1 | −9.85 | −7.02 | −7.00 |
| OVCAR-3 | −10.82 | −8.85 | −7.08 |
| OVCAR-4 | −7.85 | −7.00 | −7.00 |
| OVCAR-5 | −8.39 | −7.00 | −7.00 |
| OVCAR-8 | −9.59 | −7.48 | −7.15 |
| SK-OV-3 | −9.72 | −7.00 | −7.00 |
| Renal Cancer | | | |
| 786-0 | −10.60 | −8.92 | −7.00 |
| A498 | −10.59 | −9.11 | −7.06 |
| ACHN | −9.25 | −7.00 | −7.00 |
| CAKI-1 | −10.24 | −7.00 | −7.00 |
| RXF-393 | −10.38 | −7.00 | −7.00 |
| SN12C | −10.22 | −7.09 | −7.00 |
| TK-10 | −7.44 | −7.00 | −7.00 |
| UO-31 | −9.37 | −7.35 | −7.00 |
| Prostate Cancer | | | |
| PC-3 | −10.82 | −7.00 | −7.00 |
| DU-145 | −10.62 | −7.96 | −7.00 |
| Breast Cancer | | | |
| MCF7 | −11.00 | −7.40 | −7.00 |
| MCF7/ADR-RES | −9.04 | −8.02 | −7.35 |
| MDA-MB-231/ATCC | −9.60 | −7.64 | −7.00 |
| HS 578T | −9.36 | −7.00 | −7.00 |
| MDA-MB-435 | −11.00 | −10.47 | −8.66 |
| MDA-N | −11.00 | −11.00 | −8.14 |
| BT-549 | −9.66 | −8.00 | −8.00 |
| T-47D | −7.00 | −7.00 | −7.00 |
| MG_MID | −10.20 | −7.86 | −7.10 |
| Delta | 0.80 | 3.14 | 1.55 |
| Range | 4.00 | 4.00 | 1.66 |

TABLE 8

Human Tumor Cell Line Evaluation of Spongistatin 7

National Cancer Institute Developmental Therapeutics Program
Mean Graphs
NSC: V 3566  Units: Molar  SSPL: r  Exp. ID: Averaged
Report Date: April 15, 1993  High Conc: 1.000E-07

| Panel/Cell Line | $Log_{10}$ GI50 | GI50 | $Log_{10}$ TGI | TGI | $Log_{10}$ LC50 | LC50 |
|---|---|---|---|---|---|---|
| Leukemia | | | | | | |
| CCRF-CEM | −9.62 | | −31 7.00 | | −7.00 | |
| HL-60(TB) | −10.10 | | −8.22 | | −7.10 | |
| K-562 | −9.82 | | −7.00 | | −7.00 | |
| MOLT-4 | −9.24 | | −7.00 | | −7.00 | |
| RPMI-8226 | −9.15 | | −7.00 | | −7.00 | |
| SR | −10.04 | | 7.00 | | −7.00 | |
| Non-Small Cell Lung Cancer | | | | | | |
| A549/ATCC | −8.46 | | −7.00 | | −7.00 | |
| EKVX | −7.38 | | −7.00 | | −7.00 | |
| HOP-62 | −9.00 | | −7.28 | | −7.00 | |
| HOP-92 | −8.28 | | −7.02 | | −7.00 | |
| NCI-H226 | −8.70 | | −8.06 | | −7.00 | |
| NCI-H23 | −9.15 | | −7.39 | | −7.00 | |
| NCI-H322M | −8.49 | | −7.00 | | −7.00 | |
| NCI-H460 | −8.68 | | −7.00 | | −7.00 | |
| NCI-H522 | −10.55 | | −9.08 | | −7.00 | |
| Colon Cancer | | | | | | |
| COLO 205 | −9.48 | | −8.42 | | −7.12 | |
| HCC-2998 | −8.85 | | −7.52 | | −7.00 | |
| HCT-116 | −9.54 | | −7.19 | | −7.00 | |
| HCT-15 | −8.21 | | −7.00 | | −7.00 | |
| HT29 | −8.82 | | −7.36 | | −7.00 | |
| KM12 | −9.66 | | −7.00 | | −7.00 | |
| SW-620 | −9.41 | | −7.00 | | −7.00 | |
| CNS Cancer | | | | | | |
| SF-268 | −8.20 | | −7.00 | | −7.00 | |
| SF-295 | −9.39 | | −8.21 | | −7.00 | |
| SF-539 | −9.31 | | −8.47 | | −7.00 | |
| SNB-19 | −8.08 | | −7.00 | | −7.00 | |
| SNB-75 | −9.43 | | −7.57 | | −7.00 | |
| U251 | −9.12 | | −7.30 | | −7.00 | |
| Melanoma | | | | | | |
| LOX IMVI | −9.33 | | −7.33 | | −7.00 | |
| MALME-3M | −9.40 | | −7.00 | | −7.00 | |
| M14 | −9.31 | | −7.34 | | −7.00 | |
| SK-MEL-2 | −9.46 | | −7.00 | | −7.00 | |
| SK-MEL-28 | −8.89 | | −7.00 | | −7.00 | |
| SL-MEL-5 | −10.07 | | −7.24 | | −7.00 | |
| UACC-257 | −7.85 | | −7.00 | | −7.00 | |
| UACC-62 | −9.51 | | −7.00 | | −7.00 | |
| Ovarian Cancer | | | | | | |

TABLE 8-continued

Human Tumor Cell Line Evaluation of Spongistatin 7
National Cancer Institute Developmental Therapeutics Program
NSC: V 3566
Report Date: April 15, 1993
Units: Molar
SSPL: r    Exp. ID: Averaged
High Conc: 1.000E-07

Mean Graphs

| Panel/Cell Line | Log₁₀ GI50 | GI50 | Log₁₀ TGI | TGI | Log₁₀ LC50 | LC50 |
|---|---|---|---|---|---|---|
| IGROV1 | −9.21 | | −7.17 | | −7.00 | |
| OVCAR-3 | −10.12 | | −9.04 | | −7.32 | |
| OVCAR-4 | −7.62 | | −7.00 | | −7.00 | |
| OVCAR-5 | −7.68 | | −7.14 | | −7.00 | |
| OVCAR-8 | −8.40 | | −7.11 | | −7.00 | |
| SK-OV-3 | −9.00 | | −7.00 | | −7.00 | |
| Renal Cancer | | | | | | |
| 786-0 | −8.70 | | −7.00 | | −7.00 | |
| A498 | −8.57 | | −7.07 | | −7.00 | |
| ACHN | −8.00 | | −7.00 | | −7.00 | |
| CAKI-1 | −7.92 | | −7.40 | | −7.00 | |
| RXF-393 | −8.57 | | −7.00 | | −7.00 | |
| SN12C | −8.66 | | −7.00 | | −7.00 | |
| TK-10 | −7.25 | | −7.00 | | −7.00 | |
| UO-31 | −7.62 | | −7.02 | | −7.00 | |
| Prostate Cancer | | | | | | |
| PC-3 | −9.43 | | −7.28 | | −7.00 | |
| DU-145 | −8.80 | | −7.35 | | −7.00 | |
| Breast Cancer | | | | | | |
| MCF7 | −9.77 | | −7.00 | | −7.00 | |
| MCF7/ADR-RES | −7.11 | | −7.00 | | −7.00 | |
| MDA-MB-231/ATCC | −8.80 | | −7.25 | | −7.25 | |
| HS 578T | −8.89 | | −7.00 | | −7.00 | |
| MDA-MB-435 | −10.72 | | −9.15 | | −7.44 | |
| MDA-N | −10.82 | | −9.21 | | −7.96 | |
| BT-549 | | | −7.00 | | −7.00 | |
| T-47D | −7.00 | | −7.00 | | −7.00 | |
| MG_MID | −8.93 | | −7.34 | | −7.04 | |
| Delta | 1.90 | | 1.87 | | 0.92 | |
| Range | 3.82 | | 2.21 | | 0.96 | |

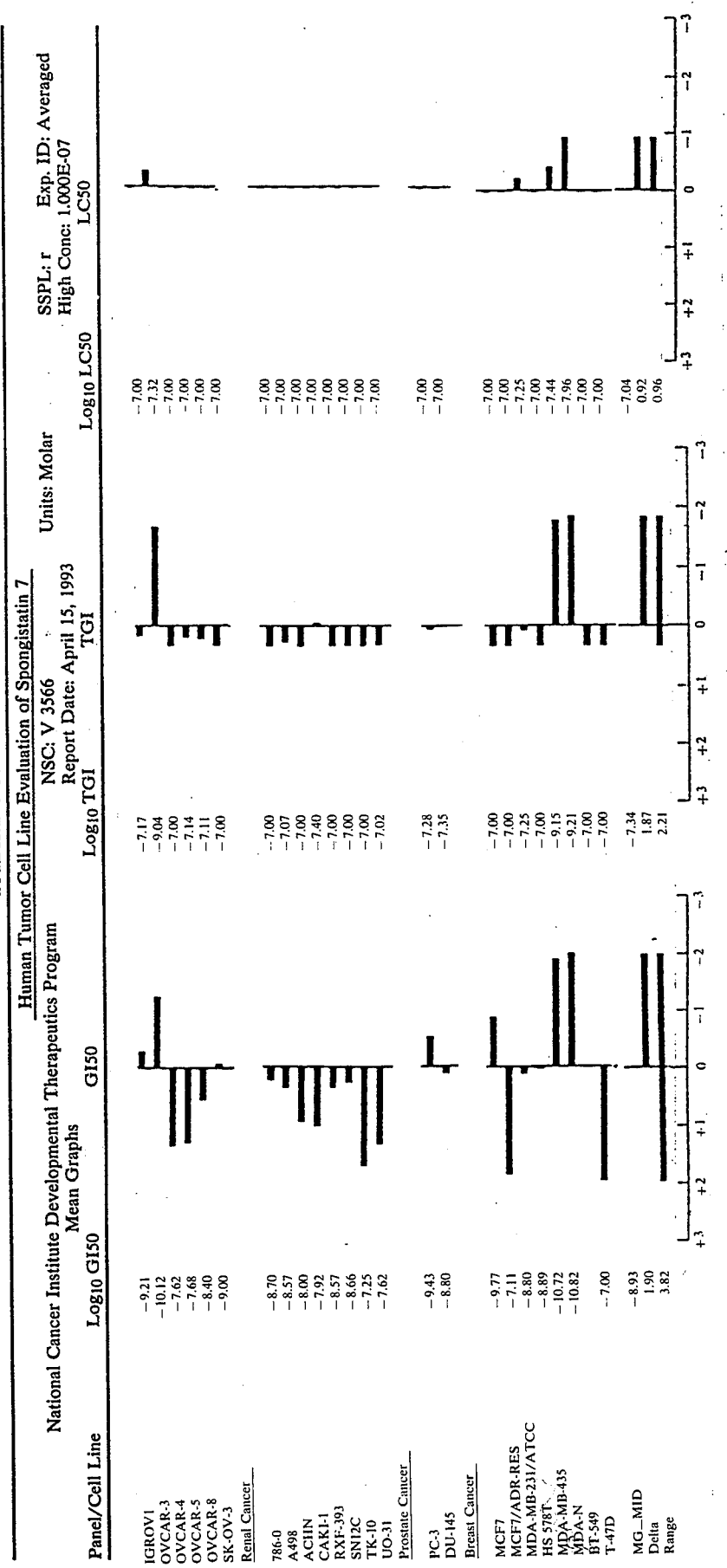

This compound can also be effectively modified with some or all of the following acids.

(a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropioplic acid and naphthylacetic acid, and the like. Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or lower alkoxy, advantageously lower alkoxy of not more than six carbon atoms, for example, methoxy, ethoxy, propoxy, butoxy, amyloxy, hexyloxy, and isomeric forms thereof. Examples of such substituted hydrocarbon carboxylic acids are: mono-, di-, and trichloroacetic acid;—and -chloropropionic acid;—and -bromobutyric acid;—and -iodovaleric acid; mevalonic acid; 2- and 4-chlorocyclohexanecarboxylic acid; shikimic acid; 2-nitro-1-methyl-cyclobutanecarboxylic acid; 1,2,3,4,5,6-hexachlorocyclohexanecarboxylic acid; 3-bromo-2-methylcyclohexanecarboxylic acid; 4- and 5-bromo-2-methylcyclohexanecarboxylic acid; 5- and 6-bromo-2-methylcyclohexanecarboxylic acid; 2,3-dibromo-2-methylcyclohexanecarboxylic acid; 2,5-dibromo-2-methylcyclohexanecarboxylic acid; 4,5-dibromo-2-methylcyclohexanecarboxylic acid; 5,6-dibromo-2-methylcyclohexanecarboxylic acid; 3-bromomethylcyclohexanecarboxylic acid; 6-bromo-3-methylcyclohexanecarboxylic acid; 1,6-dibromo-3-methylcyclohexanecarboxylic acid; 2-bromo-4-methylcyclohexanecarboxylic acid; 1,2-dibromo-4-methylcyclohexanecarboxylic acid; 3-bromo-2,2,3-trimethylcyclopentanecarboxylic acid; 1-bromo-3,5-dimethylcyclohexanecarboxylic acid; homogentisic acid, o-, m-, and p-chlorobenzoic acid; anisic acid; salicylic acid; p-hydroxybenzoic acid; b-resorcylic acid; gallic acid; veratric acid; trimethoxybenzoic acid; trimethoxycinnamic acid; 4,4'-dichlorobenzilic acid; o-, m-, and p-nitrobenzoic acid; cyanoacetic acid; 3,4- and 3,5-dinitrobenzoic acid; 2,4,6-trinitrobenzoic acid; thiocyanoacetic acid; cyanopropionic acid; lactic acid; ethoxyformic acid (ethyl hydrogen carbonate); malic acid; citric acid; isocitric acid; 6-methylsalicyclic acid; mandelic acid; levulinic acid; pyruvic acid; glycine; alanine; valine; isoleucine; leucine; phenylalanine; proline; serine; threonine; tyrosine; hydroxyproline; ornithine; lysine; arginine; histidine; hydroxylysine; phenylglycine; p-aminobenzoic acid; m-aminobenzoic acid; anthranilic acid; aspartic acid; glutamic acid; aminoadipic acid; glutamine; asparagine; and the like.

The administration of spongistatin 5, spongistatin 7, spongistatin 8 and spongistatin 9 and their pharmaceutically active, physiologically compatible derivatives is useful for treating animals or humans afflicted with a neoplastic disease, such as, for example, acute myelocytic leukemia, acute lymphocytic leukemia, malignant melanoma, adenocarcinoma of lung, neuroblastoma, small cell carcinoma of lung, breast carcinoma, colon carcinoma, gastric carcinoma, ovarian carcinoma, bladder carcinoma, hematologic malignancies and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 40 $\mu$g/kg; intramuscular, 1 to about 50 $\mu$g/kg; orally, 5 to about 100 $\mu$g/kg; intranasal instillation, 5 to about 100 $\mu$g/kg; and aerosol, 5 to about 100 $\mu$g/kg. As used herein, $\mu$g/kg means weight of active ingredient in micrograms divided by the body weight of the host in kilograms.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; and for parenteral use in a concentration of from about 0.05 to about 50% w/w of the composition and preferably from about 5 to about 20% w/w.

The composition of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling the mixture into formed gelatin sheaths. As an adjuvant to the filling operation, a lubricant such as a talc, magnesium stearate, calcium stearate and the like can be added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

When desired, each tablet can be provided with a protective coating consisting of a sealing coat or enteric coat of shellac, a coating of sugar and methylcellulose and a polish coating of carnauba wax. Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization can not be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably pyrogen free ("P.E.") water. A dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such a cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof.

EXAMPLE I

Several dosage forms can be prepared embodying the present invention. They are shown in the following examples which the notation "active ingredient" signifies spongistatin 5, spongistatin 7, spongistatin 8 and spongistatin 9 and their synthetic counterparts and the non-toxic pharmaceutically active derivatives thereof.

COMPOSITION "A"

Hard-Gelatin Capsules

One thousand two-piece hard gelatin capsules for oral use, each capsule containing 20 $\mu$g of an active ingredient are prepared from the following types and amounts of ingredients:

| | |
|---|---|
| Active ingredient, micronized | 20 mg |
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 5, 25 and 50 $\mu$g amounts by substituting 5 $\mu$m, 25 $\mu$m and 50 $\mu$m of an active ingredient for the 20 $\mu$m used above.

COMPOSITION "B"

Soft Gelatin Capsules

One-piece soft gelatin capsules for oral use, each containing 20 $\mu$g of an active ingredient (finely divided by means of an air micronizer), are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 20 μg of an active ingredient are prepared from the following types and amounts of ingredients.

| Active ingredient micronized | 20 mg |
|---|---|
| Lactose | 300 gm |
| Corn starch | 50 gm |
| Magnesium stearate | 4 gm |
| Light liquid petrolatum | 5 gm |

The active ingredient finely divided by means of an air micronizer, is added to the other ingredients and then thoroughly mixed and slugged. The slugs are broken down by forcing through a Number Sixteen screen. The resulting granules are then compressed into tablets, each tablet containing 20 μg of the active ingredient.

The foregoing tablets are useful for treating a neoplastic disease by the oral administration of one or two tablets one to four times a day.

Using the procedure above, tablets are similarly prepared containing an active ingredient in 25 μg and 10 μg amounts by substituting 25 mg and 10 mg of an active ingredient for the 20 μm used above.

COMPOSITION "D"

Oral Suspension

One thousand ml of an aqueous suspension for oral use, containing in each teaspoonful (5 ml) dose, 5 μg of an active ingredient, is prepared from the following types and amounts of ingredients:

| Active ingredient micronized | 5 mg |
|---|---|
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml | |

The citric acid, benzoic acid, sucrose, tragacanth and lemon oil are dispersed in sufficient water to make 850 ml of suspension. The active ingredient finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION "E"

Parenteral Product

A sterile aqueous suspension for parenteral injection, containing in 1 ml, 30 μg of an active ingredient for treating a neoplastic disease, is prepared from the following types and amounts of ingredients:

| Active ingredient, micronized | 30 mg |
|---|---|
| Polysorbate 80 | 5 gm |
| Methylparaben | 2.5 gm |
| Propylparaben | 0.17 gm |
| Water for injection, q.s. 1000 ml | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1M) three times a day.

COMPOSITION "F"

Suppository, Rectal and Vaginal

One thousand suppositories, each weighing 2.5 gm and containing 20 μg of an active ingredient are prepared from the following types and amounts of ingredients:

| Active ingredient, micronized | 20 mg |
|---|---|
| Propylene glycol | 150 gm |
| Polyethylene glycol #4000, q.s. | 1,500 gm |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository is foil wrapped.

The foregoing suppositories are inserted rectally or vaginally for treating a neoplastic disease.

COMPOSITION "G"

Intranasal Suspension

One thousand ml of a sterile aqueous suspension for intranasal instillation is prepared, containing 20 μg of an active ingredient per ml of suspension, from the following types and amounts of ingredients:

| Active ingredient, micronized | 30 mg |
|---|---|
| Polysorbate 80 | 5 gm |
| Methylparaben | 2.5 gm |
| Propylparaben | 0.17 gm |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times a day.

An active ingredient can also be present in the undiluted pure form for use locally about the cutis, intranasally, pharyngolaryngeally, bronchially, or orally.

COMPOSITION "H"

Powder

Five mg of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

Ten mg of an active ingredient in bulk form is finely divided by means of an air micronizer. The micronized powder is divided into individual doses of 20 µg and packaged.

The foregoing powders are useful for treating a neoplastic disease, by the oral administration of one or two powders suspended in a glass of water, one to four times per day.

COMPOSITION "J"

Insufflation

Ten mg of an active ingredient in bulk form is finely divided by means of an air micronizer.

The foregoing composition is useful for treating a neoplastic disease, by the inhalation of 30 µg one to four times per day.

COMPOSITION "K"

Hard Gelatin Capsules

One hundred two-piece hard gelatin capsules for oral use, each capsule containing 20 µg of an active ingredient.

The active ingredient is finely divided by means of an air micronizer and encapsulated in the usual manner.

The foregoing capsules are useful for treating a neoplastic disease, by the oral administration of one or two capsules, one to four times a day.

Using the procedure above, capsules are similarly prepared containing active ingredient in 5, 25 and 50 µg amounts by substituting 5 mg, 25 mg and 50 mg of the active ingredient for the 20 mg used above.

From the foregoing it is apparent that a new and useful invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended herein.

Accordingly, what is claimed is:

1. A composition of matter having the following structure:

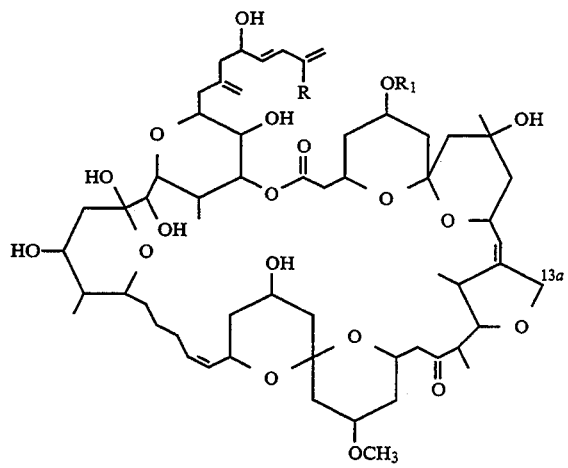

wherein $R = Cl$ or $H$ and $R_1 = H$ or $COCH_3$.

2. A composition of matter according to claim 1 wherein $R_1 = H$.

3. A composition of matter according to claim 2 wherein $R = Cl$ and said composition is denominated herein as "spongistatin 5".

4. A composition of matter according to claim 2 wherein $R = H$ and said composition is denominated herein as "spongistatin 7".

5. A composition of matter according to claim 1 wherein $R = H$ and $R_1 = COCH_3$ and said composition is denominated herein as "spongistatin 8".

6. A composition of matter according to claim 1 wherein $R = Cl$ and $R_1 = COCH_3$ and said composition is denominated herein as "spongistatin 9".

* * * * *